(12) United States Patent
Kang et al.

(10) Patent No.: US 12,150,863 B2
(45) Date of Patent: Nov. 26, 2024

(54) OBLIQUE SPINAL FUSION CAGE

(71) Applicant: L&K BIOMED CO., LTD., Yongin-si (KR)

(72) Inventors: Gook Jin Kang, Seoul (KR); Youngbo Ahn, Lone Tree, NC (US); Sang Soo Lee, Anyang-si (KR); Yun Seo Choi, Mount Eliza (AU)

(73) Assignee: L&K BIOMED CO., LTD., Yongin-si (KR)

( * ) Notice: Subject to any disclaimer, the term of this patent is extended or adjusted under 35 U.S.C. 154(b) by 188 days.

(21) Appl. No.: 17/620,558

(22) PCT Filed: Jun. 17, 2020

(86) PCT No.: PCT/KR2020/007849
§ 371 (c)(1),
(2) Date: Dec. 17, 2021

(87) PCT Pub. No.: WO2020/256410
PCT Pub. Date: Dec. 24, 2020

(65) Prior Publication Data
US 2022/0257386 A1    Aug. 18, 2022

(30) Foreign Application Priority Data
Jun. 21, 2019    (KR) .................. 10-2019-0074169

(51) Int. Cl.
*A61F 2/44*    (2006.01)
(52) U.S. Cl.
CPC .................. *A61F 2/447* (2013.01)

(58) Field of Classification Search
CPC .......... A61F 2/447; A61F 2/44; A61F 2/4611; A61F 2/4465
(Continued)

(56) References Cited

U.S. PATENT DOCUMENTS 6,143,032 A * 11/2000 Schafer ................ A61F 2/442
606/907
6,530,956 B1 * 3/2003 Mansmann ............ A61F 2/38
623/18.11
(Continued)

FOREIGN PATENT DOCUMENTS

CN        206273257 U    6/2017
CN        107773331 A    3/2018
(Continued)

OTHER PUBLICATIONS

English translation of the International Search Report in PCT/KR2020/007849, mailed Sep. 18, 2020.
(Continued)

*Primary Examiner* — Jessica Weiss
(74) *Attorney, Agent, or Firm* — MEDLER FERRO WOODHOUSE & MILLS PLLC (57) ABSTRACT

The present invention provides an oblique spinal fusion cage capable of executing a surgery even when there are a psoas muscle and a peritoneum along an operation route, which is performed in a direction inclined from a flank. The oblique spinal fusion cage has a curved shape as a whole so as to be stably seated in a space between vertebral bodies irrespective of a skill level of an operator, thereby preventing a medical accident that may occur in the patient.

6 Claims, 4 Drawing Sheets

(58) Field of Classification Search
USPC .......................................... 623/17.11–17.16
See application file for complete search history.

(56) References Cited

U.S. PATENT DOCUMENTS

| | | | |
|---|---|---|---|
| 6,579,318 B2* | 6/2003 | Varga .................... | A61F 2/4465 623/17.11 |
| 7,500,991 B2* | 3/2009 | Bartish, Jr. ........... | A61F 2/4465 623/17.11 |
| 8,382,843 B2* | 2/2013 | Laurence .............. | A61F 2/4455 623/17.16 |
| 9,474,624 B1 | 10/2016 | Ahn | |
| 9,668,876 B2 | 6/2017 | Blain et al. | |
| 9,788,967 B2 | 10/2017 | Jo | |
| 9,943,417 B2* | 4/2018 | Laurence .............. | A61F 2/4611 |
| 10,231,844 B2 | 3/2019 | Jeon et al. | |
| 10,285,823 B2 | 6/2019 | James et al. | |
| 2005/0058632 A1 | 3/2005 | Hedrick et al. | |
| 2008/0065219 A1* | 3/2008 | Dye ....................... | A61F 2/4465 623/17.16 |
| 2008/0077247 A1 | 3/2008 | Murillo et al. | |
| 2009/0210063 A1 | 8/2009 | Barrett | |
| 2010/0324690 A1 | 12/2010 | Cannon et al. | |
| 2011/0160864 A1* | 6/2011 | Messerli ................ | A61F 2/446 623/17.16 |
| 2015/0100129 A1* | 4/2015 | Waugh ............... | A61B 17/0206 623/17.16 |
| 2016/0058575 A1 | 3/2016 | Shutterlin et al. | |
| 2016/0310294 A1 | 10/2016 | McConnell et al. | |
| 2017/0042695 A1 | 2/2017 | Foley et al. | |
| 2017/0360570 A1 | 12/2017 | Berndt et al. | |
| 2018/0021149 A1 | 1/2018 | Boehm et al. | |
| 2018/0116819 A1* | 5/2018 | Maguire ............... | A61F 2/4465 |

FOREIGN PATENT DOCUMENTS

| | | |
|---|---|---|
| CN | 108742953 A | 11/2018 |
| JP | 2012-501234 A | 1/2012 |
| JP | 2014-176650 A | 9/2014 |
| JP | 2014-529466 A | 11/2014 |
| JP | 2015-521919 A | 8/2015 |
| JP | 2015-226849 A | 12/2015 |
| JP | 2019-055288 A | 4/2019 |
| KR | 10-1524532 B1 | 6/2015 |
| KR | 10-1632908 B1 | 7/2016 |
| KR | 10-2019-0056085 A | 5/2019 |
| WO | 2019/013558 A1 | 1/2019 |

OTHER PUBLICATIONS

Office Action issued in Japanese Patent Application No. 2021-57628, dated Oct. 3, 2023.
European Search Report issued in European Patent Application No. PCT/KR2020007849, dated Oct. 10, 2023.

* cited by examiner

OBLIQUE SPINAL FUSION CAGE

BACKGROUND OF THE INVENTION

1. Field of the Invention

The present invention relates to an oblique spinal fusion cage, and more specifically, to an oblique spinal fusion cage capable of executing a surgery even when there are a psoas muscle and a peritoneum along an operation route, which is performed in a direction inclined from a flank.

2. Description of the Related Art

A vertebral body includes 32 to 35 vertebrae forming a body, and intervertebral disks, i.e., spinal disks arranged between the vertebrae, and is a portion forming a backbone of a human body that connects an upper skull and a lower pelvis to form the pillar of the truncus.

The spine includes 7 cervical vertebrae, 12 thoracic vertebrae, 5 lumbar vertebrae, 5 sacral vertebrae, and 3 to 5 coccyges from the top. In the case of an adult, 5 sacral vertebrae are fused together to form one sacral vertebra, and 3 to 5 coccyges are fused together to form one tailbone.

As one of the treatment methods for treating serious spinal diseases for a long time, there is spinal fusion. Such spinal fusion is a surgical method which includes removing an intervertebral disc, and inserting a cage that replaces the intervertebral disc to fuse adjacent vertebral bodies to each other.

When performing the spinal fusion in the lumbar vertebrae, it may be divided into posterior lumbar interbody fusion (PLIF), transforaminal lumbar interbody fusion (TLIF), lateral lumbar interbody fusion (LLIF), oblique lumbar interbody fusion (OLIF), and anterior lumbar interbody fusion (ALIF) depending on an insertion direction of the cage.

The PLIF is a method which includes incising a back along a centerline of the spine, opening so as to expose all of the vertebral bodies, removing a portion of the posterior side of the vertebra, then removing the disc, and inserting a PLIF cage between the vertebrae.

The PLIF has been performed from the oldest among the spinal fusions, and is an absolutely necessary method when fusing two or three joints. However, due to a surgical process, the PLIF has various disadvantages such as high possibility of adhesion to nerves, ligaments and muscles, extended period of time for a healing time due to a large incision area, and great aftereffects for some people.

The PLIF cage is the smallest of the cages used in all spinal fusions, wherein a pair of small cages are displaced on left and right sides of the spine.

The TLIF is a surgical method which includes incising the back in a small area along both sides of a spinal muscle, exposing the vertebral bodies to a minimum, and then inserting the TLIF cage by replacing the disc while removing a spinal joint site in a direction coming out of a neuropore. This surgical technique is suitable for a case of one joint due to advantages of less bleeding, and reduced operation time. However, if an operation over multiple sites is required, the PLIF surgery should be performed. Most of the TLIF cage is formed in an arch shape, such that it is placed in the vertebral bodies and rotated so that a convex portion of the TLIF cage faces a stomach. The TLIF cage is larger than the PLIF cage, but a support area is smaller than a LLIF cage or ALIF cage which will be described below.

The ALIF has various advantages, such as fast recovery from the operation and no need to worry about adhesions. However, the ALIF has a disadvantage that highly advanced skill is needed because the operation is performed by incising an anterior (stomach) to bypass intestines, and approaching the spine. The ALIF cage has an advantage of having the largest support area among all spinal fusion cages.

The LLIF was developed to overcome the disadvantages of the ALIF, PLIF, and TLIF. Since the operation is performed through flank incision, the LLIF has advantages that an interval of stenosed sites between the vertebrae may be more greatly widened than the conventional surgeries performed by incision of the back, and there is almost no damage to surrounding tissues. However, since a psoas muscle and peritoneum are arranged around a route to be operated, there is a problem of causing thigh muscle paralysis if there is a mistake during the operation. The LLIF cage is smaller than the ALIF cage, but larger than the PLIF cage or TLIF cage.

The safer and more effective method than the LLIF is the OLIF (Oblique Lumbar Interbody Fusion) or ATP (Anterior To Psoas) fusion. The OLIF has advantages that the operation route is formed in a direction inclined from the flank, and the operation is possible between the fourth lumbar vertebra (L4) and the 5th lumbar vertebra (L5), which are difficult to operate by the DLIF due to the psoas muscle and peritoneum. In addition, the possibility of damaging the nerves, which may be a problem in the LLIF, is significantly less.

In existing oblique lumbar interbody fusion, a separate cage is not used, but a lateral lumbar interbody fusion (LLIF) cage is used. However, unlike lateral lumbar interbody fusion, when the existing LLIF cage is used for oblique lumbar interbody fusion as it is, if the LLIF cage further moves forward along an entry direction due to a slight error of an operator, a distal end (end on an insertion side) of the LLIF cage passes vertebral bodies, such that there is a risk of damaging blood vessels or nerves on a side opposite to the insertion side.

PRIOR ART DOCUMENT

[Patent Document]
(Patent Document 1) US 2016-0310294A
(Patent Document 2) U.S. Pat. No. 9,474,624
(Patent Document 3) KR 1632908B

SUMMARY OF THE INVENTION

In consideration of the above-mentioned circumstances, it is an object of the present invention to provide an oblique spinal fusion cage which may be stably seated in a space between vertebral bodies in position during a surgery, thereby preventing a medical accident.

To achieve the above object, according to an aspect of the present invention, there is provided an oblique spinal fusion cage inserted between vertebral bodies, comprising: an anterior side portion; a posterior side portion formed at a distance from the anterior side portion; a medial side portion connected to the anterior side portion and posterior side portions, at which insertion of the cage between vertebral bodies is initiated; a lateral side portion connected to the anterior side portion and the posterior side portion and coupled to a device at a position opposite to the medial side portion; and an anterior side bent portion and a posterior side bent portion formed at central portions of the anterior side portion and posterior side portion, respectively, which are bent so that centers of curvatures thereof face an anterior side, such that the posterior side bent portion, the medial side portion, and the lateral side portion are located in cortical regions of the vertebral bodies.

In the anterior side portion, anterior side straight portions, which are straight sections, may be formed between the medial side portion and the lateral side portion with the anterior side bent portion interposed therebetween, and in the posterior side portion, posterior side bent portions, which are straight sections, may be formed between the medial side portion and the lateral side portion with the posterior side bent portion interposed therebetween.

A radius of curvature R1 of the anterior side bent portion may be a radius of curvature R2 of the posterior side bent portion or less.

When a maximum distance between the anterior side straight portion and the posterior side straight portion is a width of straight portion W1, a radius of curvature R2 of the posterior side bent portion may be equal to a sum of a radius of curvature R1 of the anterior side bent portion and the width of straight portion W1.

The medial side portion may be formed in a round shape which substantially protrudes toward a medial side, and a size of a radius of curvature R3 of the medial side portion may be a size of the width of straight portion W1 or more.

A transition portion may be disposed between the medial side portion and the posterior side straight portion.

A radius of curvature R4 of the transition portion may be larger than the radius of curvature R3 of the medial side portion and smaller than the radius of curvature R2 of the posterior side portion.

A maximum height H1 of the posterior side portion may be a maximum height H2 of the anterior side portion or less.

The anterior side straight portion and the posterior side straight portion may be inclined at the same angle on both sides symmetrically about an imaginary line which connects the posterior side portion and the medial side portion.

When a maximum length of the oblique spinal fusion cage is L, and the maximum distance between the anterior side straight portion and the posterior side straight portion is the width of straight portion W1, the maximum length, the width of straight portion, and the radii of curvatures of the medial side portion and the lateral side portion may have a relationship therebetween, which satisfies the following equation:

$$0.8 \leq \frac{L \times R1}{R2 \times W1} \leq 4.5.$$

An inclination angle B° in a longitudinal direction according to the maximum length of the oblique spinal fusion cage may be obtained from the following equation, when 12≤w1≤30 and 30≤L≤90:

$$B° = \frac{180}{\pi} \times \tan^{-1}\left(\frac{W1}{L}\right).$$

According to the present invention, when inserting the inventive oblique spinal fusion cage, the cage may be seated in the space between the vertebral bodies in place regardless of skill level of an operator. That is, since the oblique spinal fusion cage has a self-centering function to find its own position by itself, it is possible to prevent blood vessels or nerves from being damaged by the medial side portion of the oblique spinal fusion cage.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, preferable embodiments of the present invention will be described with reference to the accompanying drawings. Referring to the drawings, wherein like reference characters designate like or corresponding parts throughout the several views. In the embodiments of the present invention, a detailed description of publicly known functions and configurations that are judged to be able to make the purport of the present invention unnecessarily obscure will not be described.

Figure 3:
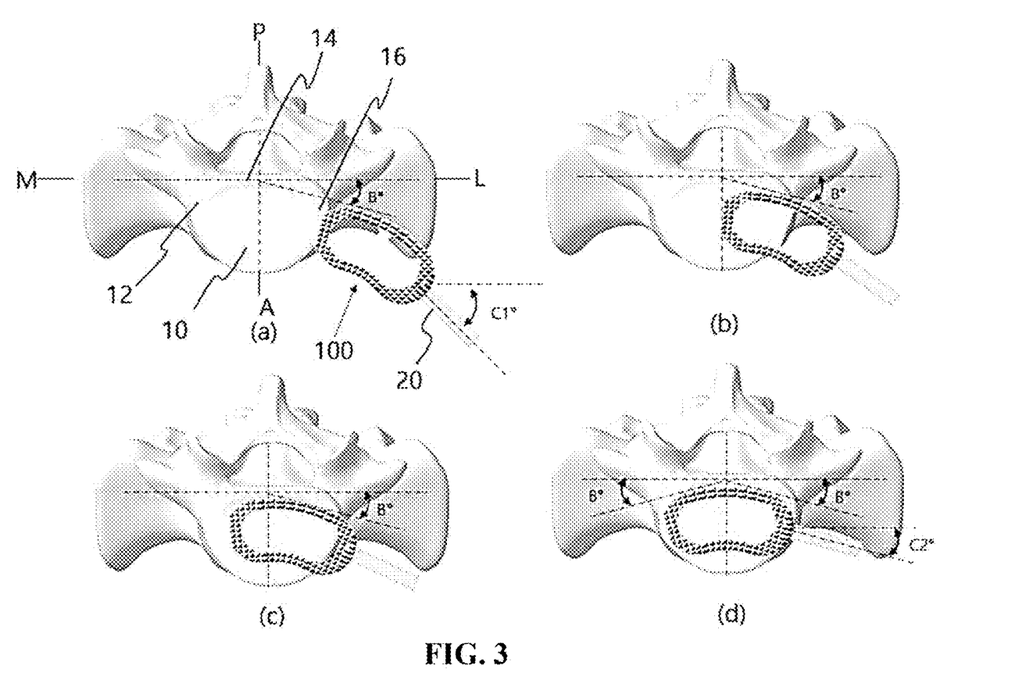
FIG. 3 is a schematic view illustrating an insertion process of the oblique spinal fusion cage of FIG. 1.
Figure 4:
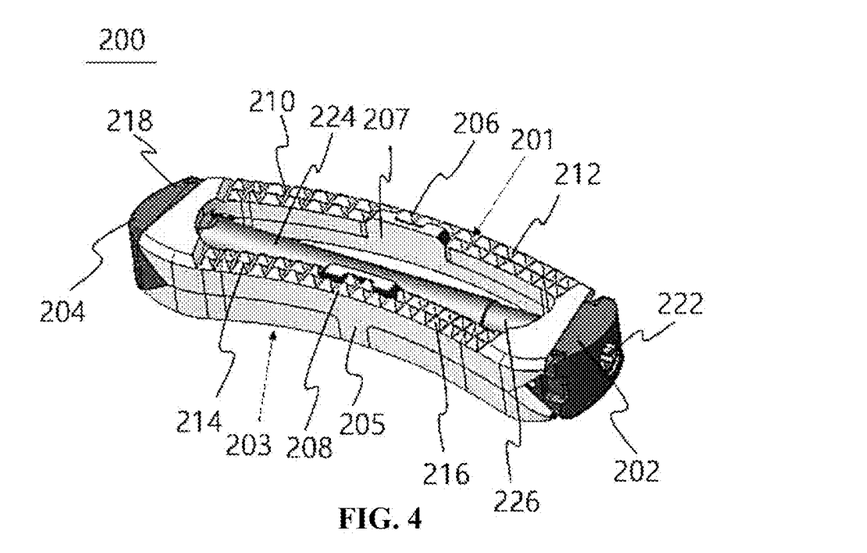
FIG. 4 is a perspective view of an oblique spinal fusion cage according to Embodiment 2 of the present invention at the lowest height state thereof.
Figure 8:
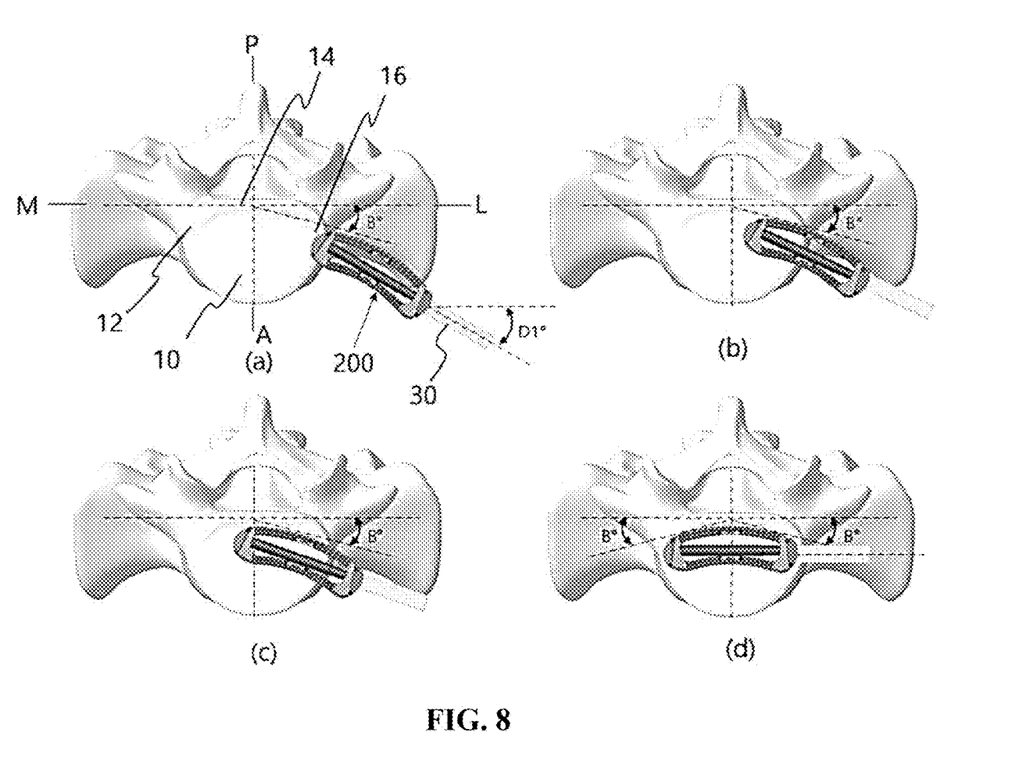
FIG. 8 is a schematic view illustrating an insertion process of the oblique spinal fusion cage of FIG. 4.

First, directions will be defined in the present disclosure. In FIGS. 3 and 8, P refers to a posterior side which is a back direction of a human body, and A refers to an anterior side which is a belly of the human body. M refers to a direction toward a medial side of the human body when viewed from an operation route, and in contrast, L refers to a direction toward a lateral side of the human body when viewed from the operation route. Further, in the cage itself, a side farther from insertion devices 20 and 30 is a distal direction, and a side close to the insertion devices 20 and 30 is a proximal direction. In other words, a side at which insertion is initiated in the cage is the distal direction, and a side opposite thereto is the proximal direction. In the following description, embodiments of the present invention will be described based on the above directions.

Figure 1:
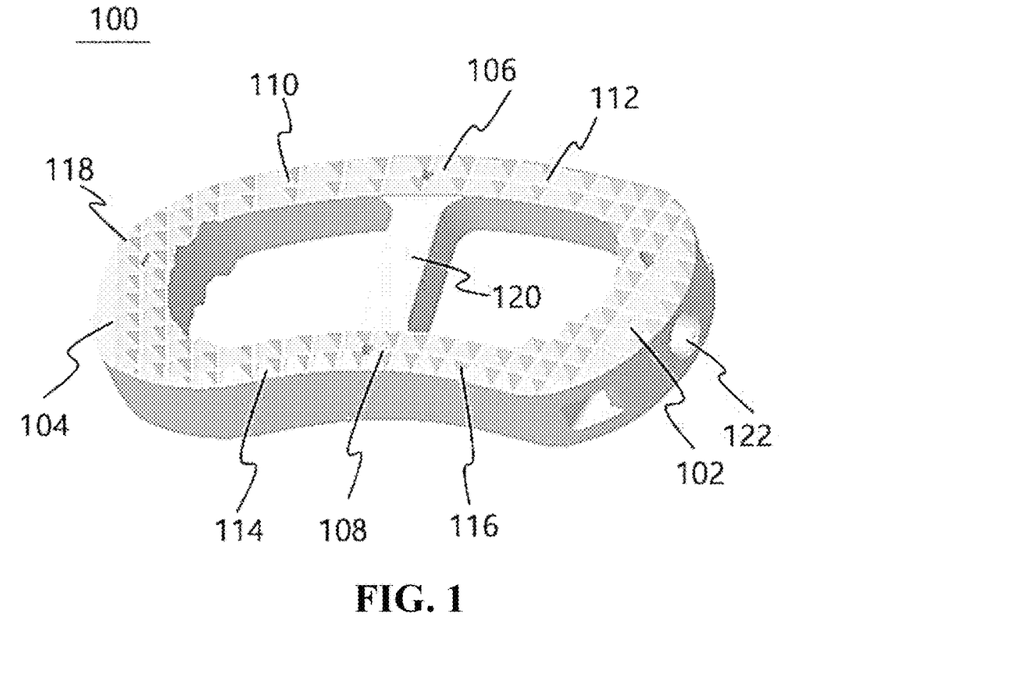
FIG. 1 is a perspective view of an oblique spinal fusion cage according to Embodiment 1 of the present invention.
Figure 2:
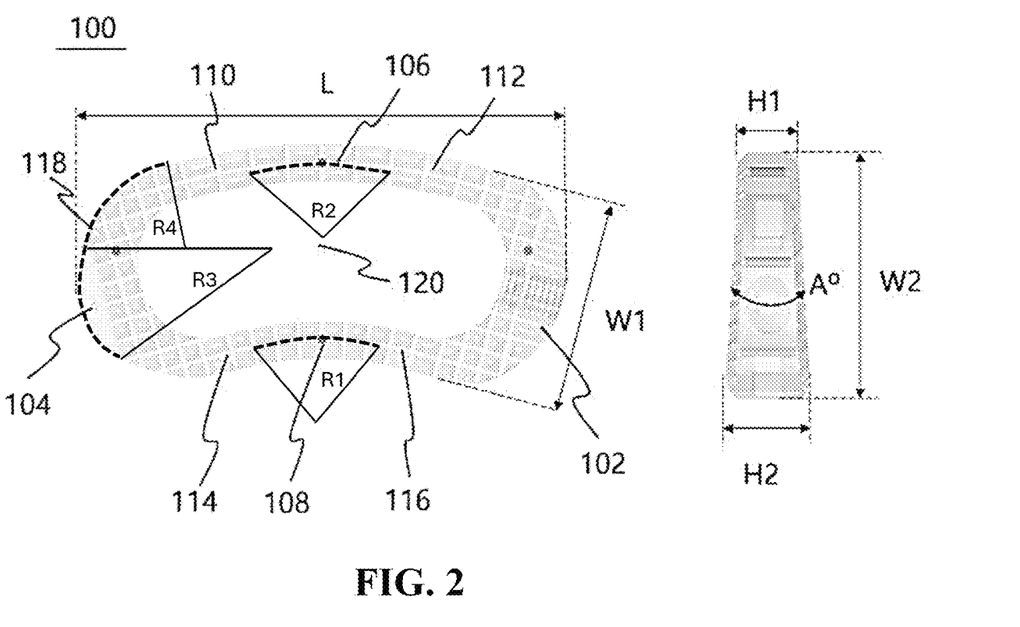
FIG. 2 is a plan view and a side view of the oblique spinal fusion cage of FIG. 1.

An oblique spinal fusion cage 100 according to Embodiment 1 of the present invention will be described with reference to FIGS. 1 to 3. As shown in FIGS. 1 and 2, the oblique spinal fusion cage 100 basically has a window into which a bone graft may be inserted, and generally includes an anterior side portion, a posterior side portion formed at a distance from the anterior side portion, a medial side portion 104 connected to the anterior side portion and the posterior side portion, at which insertion of the cage between vertebral bodies is initiated, and a lateral side portion 102 connected to the anterior side portion and the posterior side portion and coupled to the insertion device 20 at a position opposite to the medial side portion 104.

The oblique spinal fusion cage 100 may be made of a polymer material harmless to the human body, such as polyether ether ketone (PEEK), or may be formed by combining a segment of a polymer material and a segment of a metal material. In the case of metal, a metal material harmless to the human body, such as titanium and stainless steel, is used. Of course, the entire body of the cage may be made of a metal material.

Further, in the oblique spinal fusion cage 100, by using a bridge 120, it is possible to reinforce a mechanical strength thereof, and allow the bone graft inserted into the inner window to be stably located without being leaked. Further, the lateral side portion 102 has a device mounting portion 122 formed therein, to which the insertion device 20 is coupled. In Embodiment 1, the device mounting portion 122 is illustrated as a hole on which a thread is formed, but it is not limited thereto.

The greatest characteristic of the oblique spinal fusion cage 100 is that an anterior side bent portion 108 and a posterior side bent portion 106 are formed at central portions of the anterior side portion and posterior side portion, respectively, which are bent so that centers of curvatures thereof face an anterior side. Accordingly, the posterior side bent portion 106, the medial side portion, and the lateral side portion are located in cortical regions of the vertebral bodies. In other words, the oblique spinal fusion cage 100 has a curved shape so that the center of curvature is located at the anterior side as a whole. Thereby, the cage may be rotated while being inserted from the side of a flank. As a result, when the posterior side bent portion 106 is located at the center of the posterior cortical bone 14 on a posterior side of the vertebral body, the oblique spinal fusion cage 100 is seated in place. In particular, a width of the oblique spinal fusion cage 100 at the time of insertion is a width of straight portion W1 to be described below, but after it is seated in place, as shown in FIG. 2, a maximum width in an AP direction is W2, which is considerably larger than W1. As a result, the oblique spinal fusion cage 100 with a small width has a larger support area than that of the straight type cage, which will be described in more detail below.

Further, in the anterior side portion, anterior side straight portions 114 and 116, which are straight sections, are formed between the medial side portion 104 and the lateral side portion 102 with the anterior side bent portion 108 interposed therebetween, and posterior side straight portions 110 and 112, which are straight sections, may be formed between the medial side portion 104 and the lateral side portion 102 with the posterior side bent portion 106 interposed therebetween.

Accordingly, the anterior side portion includes the anterior side bent portion 108 and the anterior side straight portions 114 and 116, and the posterior side portion includes the posterior side bent portion 106 and the posterior side straight portions 110 and 112.

The anterior side straight portions 114 and 116 and the posterior side straight portions 110 and 112 facilitate insertion of the cage after the medial side portion 104 is inserted through the operation route. That is, when pushing the oblique spinal fusion cage 100 into a space between the vertebral bodies 10 by applying a force or an impact to the insertion device 20 with a hammer (not illustrated), etc., the above straight portions help the cage to be inserted in a linear direction.

In addition, it is preferable that a radius of curvature R1 of the anterior side bent portion 108 is a radius of curvature R2 of the posterior side bent portion 106 or less. That is, when inserting the oblique spinal fusion cage 100 into the space between the vertebral bodies 10, in particular, when rotating the oblique spinal fusion cage 100 in a state in which the posterior side bent portion 106 and the anterior side bent portion 108 are inserted, it is desirable to increase an amount of rotation by inserting the anterior side portion more than the posterior side portion. Therefore, the radius of curvature R1 of the anterior side bent portion 108 should be smaller than the radius of curvature R2 of the posterior side bent portion 106.

At this time, when a maximum distance between the anterior side straight portions 114 and 116 and the posterior side straight portions 110 and 112 is the width of straight portion W1, the radius of curvature R2 of the posterior side bent portion 106 may be set equal to a sum of the radius of curvature R1 of the anterior side bent portion 108 and the width of straight portion W1. That is, it may be deemed that, if the posterior side portion substantially passes more than the anterior side portion by the width of straight portion W1, it is sufficient to rotate the oblique spinal fusion cage 100 with the above-described amount of rotation thereof. Herein, when considering a size of a general vertebral body, it may be determined that the width W1 is from 12 to 30 mm, and preferably 18 to 24 mm. In addition, it may be determined that the radius of curvature R2 is from 30 to 100 mm, and preferably 40 to 85 mm.

Further, the medial side portion 104 may be formed in a round shape which substantially protrudes toward the medial side. This is to facilitate insertion of the oblique spinal fusion cage 100 at the time of initial insertion, and a size of the radius of curvature R3 of the medial side portion 104 is a size of the width of straight portion W1 or more. In other words, the most prominently convex medial side portion 104 is a semicircular shape having a diameter of the width of straight portion W1, and may be formed more bluntly than the same.

The radius of curvature R1 of the anterior side portion and the radius of curvature R2 of the posterior side portion described above may be obtained by an empirical equation as follows. That is, when the maximum length of the oblique spinal fusion cage 100 is L, and the maximum distance between the anterior side straight portions 114 and 116 and the posterior side straight portions 110 and 112 is the width of straight portion W1, it is characterized in that the maximum length, the width of straight portion, and the radii of curvatures of the medial side portion and the lateral side portion have a relationship therebetween, which satisfies the following equation. In the equation below, L is determined from 30 to 90 mm, and preferably from 40 to 65 mm.

$$0.8 \leq \frac{L \times R1}{R2 \times W1} \leq 4.5$$

In addition, a transition portion 118 may be disposed between the medial side portion 104 and the posterior side straight portion 110. The transition portion 118 serves to facilitate the oblique spinal fusion cage 100 to be rotated while being into contact with a posterior side hard bone 14 when the medial side portion 104 is initially inserted and gradually enters. To this end, it is preferable that the transition portion 118 is formed with a radius of curvature R4 which is larger than the radius of curvature R3 of the medial side portion and smaller than the radius of curvature R2 of the posterior side portion.

In addition, it is preferable that a maximum height H1 of the posterior side portion is a maximum height H2 of the anterior side portion or less. In the spine, lordosis and kyphosis are generally repeated, and the lumbar vertebrae has a form of lordosis. Accordingly, in order to cope with this form, the posterior side portion should be formed to have a height lower than that of the anterior side portion. In addition, if a lordosis angle A° is formed by a height difference between the posterior side portion and anterior side portion, when the oblique spinal fusion cage 100 is inserted by the insertion device 20, there is an advantage that the oblique spinal fusion cage 100 is biased to the posterior side like a wedge due to a force applied thereto.

Further, the anterior side straight portions 114 and 116 and the posterior side straight portions 110 and 112 may be formed to be inclined at the same angle on both sides symmetrically about an imaginary line (line AP) which connects the posterior side portion and the medial side portion. Therefore, in addition to the ease of insertion, there are characteristics in which, after the insertion is finally completed, the oblique spinal fusion cage 100 is disposed symmetrically about the AP line, thus to be anatomically stable.

In addition, an inclination angle B° with respect to the maximum length L of the oblique spinal fusion cage 100 may be obtained from the following equation, when 12≤w1≤30 and 30≤L≤90.

$$B° = \frac{180}{\pi} \times \tan^{-1}\left(\frac{W1}{L}\right)$$

The inclination angle B° not only determines a shape of the oblique spinal fusion cage 100, but also determines a direction in which the cage is initially inserted into the vertebral bodies 10. The inclination angle B° indicated in FIGS. 3 and 8 is 15°, and is determined between about 8° and 45°.

Next, an insertion process of the cage will be described with reference to FIG. 3. First, as shown in FIG. 3(a), the insertion device 20 is coupled with the oblique spinal fusion cage 100 and inserted so that an insertion angle is the inclination angle B°. At this time, an inclination angle C1° formed by the insertion device 20 with the ML line is not separately adjusted, but is determined according to the direction in which the device mounting portion 122 of the oblique spinal fusion cage 100 is formed.

In addition, as shown in FIGS. 3(b) and (c), the oblique spinal fusion cage 100 is rotated, while continuously inserting the oblique spinal fusion cage 100 into the space between the vertebral bodies 10. Rotation of the cage may be performed by pushing the insertion device 20 to the posterior side. At this time, as described above, the transition portion 118 connected to the medial side portion 104 comes into contact with the posterior side hard bone 14 to guide the rotation of the oblique spinal fusion cage 100.

Finally, when the insertion of the cage is completed, as shown in FIG. 3(d), the oblique spinal fusion cage 100 is located to be inclined at the same angle on both sides about the AP line thereof. As a result, the medial side portion 104 is located at a medial side hard bone 12, the lateral side portion 102 is located at a lateral side hard bone 16, and the posterior side bent portion 106 is located at the posterior side hard bone 14.

Next, an oblique spinal fusion cage 200 according to Embodiment 2 of the present invention will be described with reference to FIGS. 4 to 8. The oblique spinal fusion cage 200 has the same shape as the oblique spinal fusion cage 100 of Embodiment 1 except that it is an expandable cage whose height is adjustable. Although different symbols are denoted, the same components will not be described.

As shown in FIGS. 4 to 7, the oblique spinal fusion cage 200 basically has an upper plate 201 and a lower plate 203, and a lateral side portion 202 and a medial side portion 204 are located between the upper plate 201 and the lower plate 203. In addition, a fixing screw 224 integrally connected to the medial side portion 204 and a driving screw 226 supported so as to be rotatable through the lateral side portion 202 are located in a straight line. Accordingly, when the driving screw 226 rotates and is coupled with the fixing screw 224, a distance between the lateral side portion 202 and the medial side portion 204 is decreased, and as a result, the heights of the upper plate 201 and the lower plate 203 may be changed. Rails (not illustrated) are formed between the lateral side portion 202, the medial side portion 204, the upper plate 201, and the lower plate 203 for mutually moving therebetween.

However, in order to prevent the upper plate 201 and the lower plate 203 from moving in a vertical direction, upper guides 205 and lower guides 207 may be formed on the upper plate 201 and the lower plate 203, respectively.

This embodiment is the same as Embodiment 1 in an aspect that the oblique spinal fusion cage 200 has a window into which a bone graft may be inserted, and generally includes an anterior side portion, a posterior side portion formed at a distance from the anterior side portion, a medial side portion 104 connected to the anterior side portion and the posterior side portion, at which insertion of the cage between vertebral bodies is initiated, and a lateral side portion 102 connected to the anterior side portion and the posterior side portion and coupled to the insertion device 20 at a position opposite to the medial side portion 104.

The oblique spinal fusion cage 200 is basically made of a metal material such as titanium and stainless steel, but may be made of a polymer material harmless to the human body such as polyether ether ketone (PEEK). Alternately, metal and polymer material may be differently used for each component.

In addition, the lateral side portion 202 has a device mounting portion 222 formed therein, to which an insertion device 30 is coupled. In Embodiment 2, the device mounting portion 222 is illustrated in a shape of a tool groove formed in a head portion of the driving screw 226, but it is not limited thereto. Although not illustrated in the drawings, the insertion device 30 may further include a gripper, etc., for firmly coupling with the oblique spinal fusion cage 200.

The oblique spinal fusion cage 200 further includes an anterior side bent portion 208 and a posterior side bent portion 206 at the central portions of the anterior side portion and posterior side portion, respectively, which are bent so that centers of curvatures thereof face the anterior side.

Further, it is the same as that of the oblique spinal fusion cage 100 of Embodiment 1 in an aspect that, in the anterior side portion, anterior side straight portions 214 and 216, which are straight sections, are formed between the medial side portion 204 and the lateral side portion 202 with the anterior side bent portion 208 interposed therebetween, and posterior side straight portions 210 and 212, which are straight sections, may be formed between the medial side portion 204 and the lateral side portion 202 with the posterior side bent portion 206 interposed therebetween.

In addition, a transition portion 218 may be disposed between the medial side portion 204 and the posterior side straight portion 210.

Further, it is the same as that of the oblique spinal fusion cage 100 of Embodiment 1 in an aspect that the maximum height H1 of the posterior side portion is the maximum height H2 of the anterior side portion or less.

Next, an insertion process of the cage will be described with reference to FIG. 8. First, as shown in FIG. 8(a), the insertion device 30 is coupled with the oblique spinal fusion cage 200 and inserted so that an insertion angle is the inclination angle B°. At this time, an inclination angle C1° formed by the insertion device 30 with the ML line is not separately adjusted, but is determined according to the direction in which the device mounting portion 222 of the oblique spinal fusion cage 200 is formed.

And, as shown in FIGS. 8(b) and (c), the oblique spinal fusion cage 200 is rotated, while continuously inserting the oblique spinal fusion cage 200 into the space between the vertebral bodies 10. Rotation of the cage may be performed by pushing the insertion device 30 to the posterior side. At this time, as described above, the transition portion 218 connected to the medial side portion 204 comes into contact with the posterior side hard bone 14 to guide the rotation of the oblique spinal fusion cage 200.

Finally, when the insertion of the cage is completed, as shown in FIG. 8(d), the oblique spinal fusion cage 200 is located to be inclined at the same angle on both sides about the AP line thereof. As a result, the medial side portion 204 is located at a medial side hard bone 12, the lateral side portion 202 is located at a lateral side hard bone 16, and the posterior side bent portion 206 is located at the posterior side hard bone 14.

Figure 5:
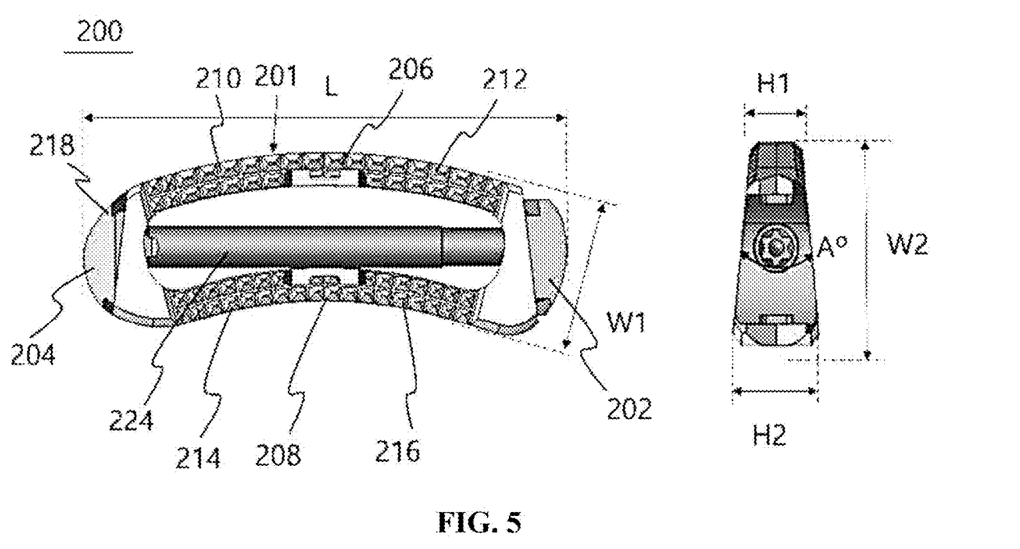
FIG. 5 is a plan view and a side view of the oblique spinal fusion cage of FIG. 4.
Figure 6:
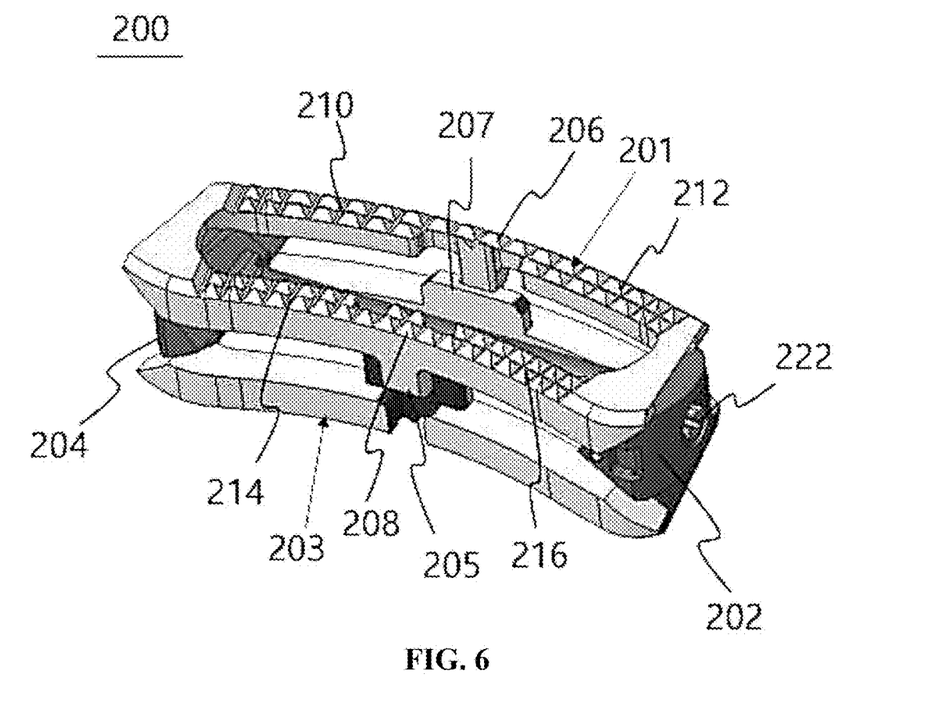
FIG. 6 is a perspective view of the oblique spinal fusion cage of FIG. 4 in the highest height state thereof.
Figure 7:
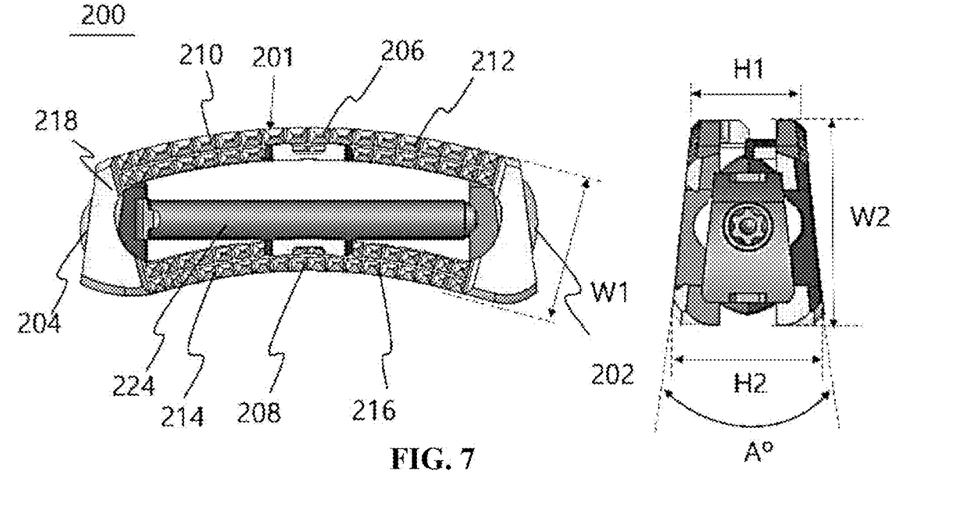
FIG. 7 is a plan view and a side view of the oblique spinal fusion cage of FIG. 6.

In addition, since the oblique spinal fusion cage 200 of Embodiment 2 is an inflatable cage, the cage has the lowest height as shown in FIG. 5 at the time of initial insertion. However, when rotating the driving screw 226, the distance between the upper plate 201 and the lower plate 203 is changed as described above, and the height may be changed as shown in FIG. 7.

While the present invention has been described with reference to the preferred embodiments and modified examples, the present invention is not limited to the above-described specific embodiments and the modified examples, and it will be understood by those skilled in the art that various modifications and variations may be made therein without departing from the scope of the present invention as defined by the appended claims.

INDUSTRIAL APPLICABILITY

The oblique spinal fusion cage according to the present invention may be stably seated in the space between the vertebral bodies irrespective of a skill level of an operator, thereby preventing a medical accident that may occur in the patient. In addition, since such a stable seating is ensured, it is possible to replace other methods of spinal fusions by simply educating the operator. Therefore, it is expected that the market share can be increased.

DESCRIPTION OF REFERENCE NUMERALS

10: Vertebral body
12: Medial side hard bone
14: Posterior side hard bone
16: Lateral side hard bone
20, 30: Insertion device
100, 200: Oblique spinal fusion cage
102, 202: Lateral side portion
104, 204: Medial side portion
106, 206: Posterior side bent portion
108, 208: Anterior side bent portion
110, 112, 210, 212: Posterior side straight portion
114, 116, 214, 216: Anterior side straight portion
118, 218: Transition portion
120: Bridge
122, 222: Device mounting portion
201: Upper plate
203: Lower plate
205: Upper guide
207: Lower guide
224: Fixing screw
226: Driving screw

What is claimed is:

1. An oblique spinal fusion cage configured to be inserted between vertebral bodies, comprising:
   an anterior side portion;
   a posterior side portion formed at a distance from the anterior side portion;
   a medial side portion connected to the anterior side portion and the posterior side portion, at which insertion of the cage between vertebral bodies is initiated;
   a lateral side portion connected to the anterior side portion and the posterior side portion, the lateral side portion configured to couple to an implant device; and
   an anterior side bent portion and a posterior side bent portion formed at central portions of the anterior side portion and the posterior side portion, respectively, which are bent so that centers of curvatures thereof are configured to face an anterior side of a patient, such that the posterior side bent portion, the medial side portion, and the lateral side portion are configured to be located in cortical regions of the vertebral bodies, wherein, in the anterior side portion, anterior side straight portions, which are straight sections, are formed between the medial side portion and the lateral side portion with the anterior side bent portion interposed therebetween, and
   in the posterior side portion, posterior side straight portions, which are straight sections, are formed between the medial side portion and the lateral side portion with the posterior side bent portion interposed therebetween, and
   wherein the anterior side straight portions and the posterior side straight portions are symmetrically disposed about an imaginary line which extends through centers of the posterior side bent portion and the anterior side bent portion,
   wherein when a maximum distance between an outer edge of an anterior side straight portion of the anterior side straight portions and an outer edge of a corresponding posterior side straight portion of the posterior side straight portions is a width W1, a radius of curvature R2 of the posterior side bent portion is equal to a sum of a radius of curvature R1 of the anterior side bent portion and the width W1, and
   wherein the medial side portion is rounded, and a radius of curvature R3 of the medial side portion is equal to or greater than the width W1.

2. The oblique spinal fusion cage according to claim 1, wherein the radius of curvature R1 of the anterior side bent portion is less than the radius of curvature R2 of the posterior side bent portion.

3. The oblique spinal fusion cage according to claim 1, wherein a transition portion is disposed between the medial side portion and an adjacent posterior side straight portion of the posterior side straight portions.

4. The oblique spinal fusion cage according to claim 3, wherein a radius of curvature R4 of the transition portion is larger than the radius of curvature R3 of the medial side portion and smaller than the radius of curvature R2 of the posterior side portion.

5. The oblique spinal fusion cage according to claim 1, wherein a maximum height H1 of the posterior side portion is equal to or less than a maximum height H2 of the anterior side portion.

6. The oblique spinal fusion cage according to claim 1, wherein, a relationship between a maximum length L of the oblique spinal fusion cage, the width W1, the radius of curvature R1 of the anterior side bent portion and the radius of curvature R2 of the posterior side bent portion is based on the following equation:

$$0.8 \leq \frac{L \times R1}{R2 \times W1} \leq 4.5.$$

* * * * *